United States Patent
Adamson et al.

(10) Patent No.: US 9,978,172 B2
(45) Date of Patent: May 22, 2018

(54) METHOD FOR RECORDING INDIVIDUAL THREE-DIMENSIONAL OPTICAL IMAGES TO FORM A GLOBAL IMAGE OF A TOOTH SITUATION

(71) Applicant: DENTSPLY SIRONA Inc., York, PA (US)

(72) Inventors: Anders Adamson, Darmstadt (DE); Burkhard Lehner, Radolfzell (DE); Joost Sattler, Bensheim (DE); Tom Bobach, Bensheim (DE); Frank Thiel, Ober-Ramstadt (DE)

(73) Assignee: DENTSPLY SIRONA INC., York, PA (US)

( * ) Notice: Subject to any disclaimer, the term of this patent is extended or adjusted under 35 U.S.C. 154(b) by 0 days. days.

(21) Appl. No.: 14/421,219

(22) PCT Filed: Aug. 14, 2013

(86) PCT No.: PCT/EP2013/066993
§ 371 (c)(1),
(2) Date: Feb. 12, 2015

(87) PCT Pub. No.: WO2014/027024
PCT Pub. Date: Feb. 20, 2014

(65) Prior Publication Data
US 2015/0235412 A1    Aug. 20, 2015

(30) Foreign Application Priority Data
Aug. 14, 2012 (DE) .................. 10 2012 214 470

(51) Int. Cl.
*G06T 17/00* (2006.01)
*A61C 9/00* (2006.01)
(Continued)

(52) U.S. Cl.
CPC ............ *G06T 17/00* (2013.01); *A61C 9/0053* (2013.01); *G06T 7/0032* (2013.01); *G06T 15/20* (2013.01);
(Continued)

(58) Field of Classification Search
CPC ......... A61C 11/00; A61C 19/04; A61C 9/004; A61C 9/0053; A61C 7/002;
(Continued)

(56) References Cited

U.S. PATENT DOCUMENTS 5,683,243 A * 11/1997 Andreiko ................. A61C 7/00
433/24
6,152,731 A    11/2000 Jordan et al.
(Continued)

FOREIGN PATENT DOCUMENTS

DE        10252298 B3    8/2004
DE    102004038136 A1    2/2006
(Continued)

OTHER PUBLICATIONS

International Search Report dated Dec. 6, 2014, in PCT Application No. PCT/EP2013/066993.
(Continued)

*Primary Examiner* — Kim Vu
*Assistant Examiner* — Michael Vanchy, Jr.
(74) *Attorney, Agent, or Firm* — David A. Zdurne; Douglas J. Hura; Leana Levin

(57) ABSTRACT

The invention relates to a method for recording individual three-dimensional optical images (1) to form a global image (50) of a tooth situation comprising an upper jaw (2) and a lower jaw (3). A first 3D model (6) of a first subsection of the upper jaw and a second 3D model (8) of a second subsection of the lower jaw are produced from the individual images. Subsequently, a geometric positional relationship (Continued)

between the first 3D model (6) and the second 3D model (8) is determined, said positional relationship being determined by using a lateral image (20, 21, 22) and/or using a contact pattern (31, 32). Said lateral image (20, 21, 22) comprises an image area which comprises at least part of the first subsection of the upper jaw (2) and at least part of the second subsection of the lower jaw (3). Said contact pattern comprises several contact areas (31, 32) between the upper jaw and the lower jaw. Said contact pattern (30, 31, 32) is measured by means of an occlusion paper (29).

22 Claims, 3 Drawing Sheets

(51) Int. Cl.
*G06T 7/00* (2017.01)
*G06T 19/00* (2011.01)
*G06T 15/20* (2011.01)
(52) U.S. Cl.
CPC .......... *G06T 19/00* (2013.01); *G06T 2210/32* (2013.01); *G06T 2210/41* (2013.01); *G06T 2219/016* (2013.01); *G06T 2219/2008* (2013.01); *G06T 2219/2021* (2013.01)
(58) Field of Classification Search
CPC ....... A61C 13/0004; A61C 7/00; A61C 7/146; A61C 19/05; A61C 9/0046; A61C 13/097; A61C 2007/004; A61C 7/16; A61C 7/20; A61C 9/00; A61C 9/0006; A61C 11/005; A61C 13/0013; A61C 19/045; A61C 1/084; A61C 7/12; A61C 7/145; A61C 8/009; A61C 9/006; A61C 9/0086; G06T 19/00; G06T 17/00; G06T 2207/30036; G06T 7/0032; A61B 6/14; A61B 5/4547; A61B 1/00009; A61B 2090/365; A61B 5/1079
See application file for complete search history.

(56) References Cited

U.S. PATENT DOCUMENTS

| | | | |
|---|---|---|---|
| 6,582,229 B1 | 6/2003 | Miller et al. | |
| 7,801,632 B2 | 9/2010 | Orth et al. | |
| 8,727,776 B2 | 5/2014 | Mehl | |
| 2002/0015934 A1* | 2/2002 | Rubbert | A61C 7/00 433/29 |
| 2008/0176182 A1* | 7/2008 | Hultgren | A61C 11/00 433/69 |
| 2009/0086886 A1* | 4/2009 | Akahori | A61B 6/025 378/11 |
| 2011/0045428 A1* | 2/2011 | Boltunov | A61C 7/002 433/24 |
| 2012/0040311 A1* | 2/2012 | Nilsson | A61C 19/05 433/214 |
| 2012/0121156 A1* | 5/2012 | Hwang | A61B 6/14 382/131 |

FOREIGN PATENT DOCUMENTS

| | | |
|---|---|---|
| DE | 69837442 T2 | 12/2007 |
| WO | 2010105837 A1 | 9/2010 |

OTHER PUBLICATIONS

International Preliminary Report on Patentability dated Nov. 12, 2014, in PCT Application No. PCT/EP2013/066993.
Written Opinion of the International Searching Authority, PCT/EP/2013/066993.
Office Action, German Patent Appln. No. 10 2012 214 470.6, dated Apr. 8, 2013.

\* cited by examiner

METHOD FOR RECORDING INDIVIDUAL THREE-DIMENSIONAL OPTICAL IMAGES TO FORM A GLOBAL IMAGE OF A TOOTH SITUATION

TECHNICAL FIELD

The invention relates to a method for recording individual three-dimensional optical images to form a global image of a tooth situation comprising an upper jaw and lower jaw, wherein a first 3D model of a first subsection of the upper jaw, and a second 3D model of a second subsection of the lower jaw, are generated from the individual images.

PRIOR ART

A number of registration methods are already known from the prior art in which individual sequentially-recorded, three-dimensional optical images are combined into a global image. Corresponding areas in the individual images are detected and overlapped. These areas are also termed overlapping areas. However, registration errors can arise during registration that are caused by excessively small overlapping areas from imaging flaws or from faulty registration algorithms. As a consequence of these registration errors, the generated global image deviates from the actual dimensions of the imaged object. This registration error increases as the length of a registration chain from the individual images increases.

This has the disadvantage that the registration error can lead to faulty planning of the dental prosthesis to be produced.

The object of the present invention is hence to provide a registration method for determining a positional relationship between the individual images that reduces the registration error in order to produce a fitting dental prosthesis using to the generated global image.

DESCRIPTION OF THE INVENTION

The invention relates to a method for recording individual three-dimensional optical images to form a global image of a tooth situation comprising an upper jaw and a lower jaw. In so doing, a first 3D model of a first subsection of the upper jaw and a second 3D model of a second subsection of the lower jaw are generated from the individual images. Then a geometric positional relationship is determined between the first 3D model and the second 3D model. The positional relationship is determined using a lateral image and/or using a contact pattern. The lateral image has an image area that at least partially comprises the first subsection of the upper jaw, and at least partially comprises the second subsection of the lower jaw. The contact pattern comprises a plurality of contact areas between the upper jaw and lower jaw. The contact pattern is measured using occlusion paper by placing the occlusion paper between the upper jaw and lower jaw, and then bringing the upper jaw and lower jaw into a closed-bite position. Then, after the occlusion paper has been removed, the individual images are measured in order to record the contact areas of the contact pattern on the upper jaw and lower jaw. Then the generated first 3D model and the generated second 3D model are analyzed by means of a computer in order to determine the position of the contact areas.

The optical measurement can for example be performed by a dental camera based on a strip projection method, a confocal optical method, or a color strip projection method.

In the color strip projection method, a pattern consisting of a number of colored strips is projected onto the object. Then the depth coordinates for the measured points are determined, and a 3D model of the object is generated. The colored strips can be clearly identified by their color. Four colored strips and three color transitions can, for example, be used for color-coding the colored strips. The colored strips can for example be generated using a slide.

For the optical measurement, a different strip projection method can also be used in which the strips are coded using different optical properties such as intensity, color, polarization, coherence, phase, contrast, location or propagation time.

The strip width of such strip projection methods can for example be 130 µm in the measured volume of the object to be measured.

A so-called confocal chromatic triangulation method can also be used for the measurement in which the concepts of confocal measurement and triangulation measurement are combined with each other. The basic idea consists of coloring the surface of an object so that the height coordinate can be directly inferred from a color. The colors are generated by a spectral splitting of the projected light, and each wavelength is focused on its own height coordinate.

During the measurement, the hand-held digital camera is moved relative to the dental object such as a lower jaw or an upper jaw during which the three-dimensional optical images are generated at regular intervals in time. The individual images can for example be generated at a cyclical frequency between 10 Hz and 20 Hz. Then the individual images are recorded using a computer and combined into a global image.

In the first step, a subsection of the upper jaw or the entire upper jaw is thus measured, and the first 3D model is generated therefrom. In the second step, the second subsection of the lower jaw or the entire lower jaw is measured, and the second 3D module is generated by registration. The first 3D model and/or the second 3D model can, however, be distorted by the registration error, or by a calibration error in comparison to the actual dimensions of the measured object. The calibration error can for example be caused by faulty settings of camera parameters of the dental camera. With a dental camera based on the strip projection method, the relevant camera parameters are the distance between the camera and the object being measured, the angle of incidence, as well as the grid interval of a grid to generate a strip pattern.

The camera parameters can also be based on a pinhole camera model, wherein a distinction is drawn between intrinsic and extrinsic. Possible intrinsic parameters are for example the focal length of the camera, the pixel coordinates of the image center, and list parameters. The extrinsic parameters can comprise the rotation and translation between the camera and projector.

The registration error can for example be caused by the following factors: An excessively small overlapping area, insufficient waviness of the object surface in the overlapping area, insufficient roughness of the object surface in the overlapping area, an insufficient number of characteristic geometries in the overlapping area such as dental protuberances or fissures, and/or defective image quality in the overlapping area. The registration is for example faulty in those instances when the dental camera moves too quickly in relation to the object, which causes the size of the overlapping area to be insufficient. Another reason could be that the autofocus of the digital camera is not sharply set, thus causing the object to be indistinctly imaged such that the quality of the image is insufficient. An additional reason could be that movable objects such as the tongue of the patient or a finger of the treating dentist are recorded during measurement. Consequently, the overlapping areas of the images do not correspond. The cited reasons could hence lead to a distorted first 3D model of the upper jaw and/or a distorted second 3D model of the lower jaw in comparison to the object.

The geometric positional relationship between the first 3D model and the second 3D model is hence determined using the lateral image and/or using the contact pattern.

The lateral image can for example be made from a labial direction, or a buccal direction, or at a slight angle thereto. It is key for the lateral image to comprise at least parts of the first subsection of the upper jaw and the second subsection of the lower jaw. The lateral image thereby makes it possible to determine the positional relationship between the first 3D model and the second 3D module, aided by characteristic structures of the upper jaw and lower jaw, or with the help of markers placed on the teeth. In addition to the first lateral image, additional lateral images can also be created from different directions in order to check the positional relationship of different areas of the 3D models. The lateral image, or the buccal image, can for example be taken in the area of teeth 14, 44 or 24, 34, respectively, according to the FDI notation.

The contact pattern can for example be measured using an occlusion paper, wherein the contact areas or contact points between the upper jaw and lower jaw are recorded in a closed-bite position. The precise positional relationship between the first 3D model of the upper jaw and the second 3D model of lower jaw can then be determined with the aid of these contact areas.

The occlusion paper makes it possible to measure the proximal contact or contact areas of the contact pattern between the upper jaw and lower jaw in the closed-bite position. The positional relationship between the first 3D model and the second 3D model can then be determined with the assistance of a computer, while using the generated contact pattern. This is done by simulating the contact areas at which the upper jaw come into contact with the lower jaw in closed-bite position using the measured contact pattern, and using the geometries of the first 3D model and second 3D model. As a result of this simulation, it is determined in the next step precisely where the virtual contact areas are arranged on the first 3D model and the second 3D model. Subsequently, the positional relationship between the first 3D model and second 3D model is then established by overlapping the corresponding virtual contact areas of the two 3D models, or minimizing the distance between the contact areas.

An advantage of this method is that a check of the generated 3D models is easily enabled using the lateral image and/or using the contact pattern. This minimizes the registration error and/or the calibration error.

Advantageously, additional lateral images can be used to determine the positional relationship.

This makes it possible to check the positional relationship of primary areas of the upper jaw or lower jaw. The lateral images can be taken from a number of directions, such as for tooth pairs 14-44, 11-41 and 24-34 according to the FDI notation. The lateral images can be taken from a labial or buccal direction, or from an oblique direction that is at a maximum angle of 30° to the labial direction.

To determine the positional relationship using a pattern recognition method, the lateral image can advantageously be searched for a first surface structure from the first 3D model, and for a second surface structure consisting of the second 3D model, wherein the positional relationship between the first 3D model and the second 3D model is determined with the aid of arrangement of the first surface structure relative to the second surface structure in the lateral image.

The first surface structure and second surface structure can be characteristic structures of the upper jaw or the lower jaw such as certain teeth, gingiva structures or marks applied to the teeth. The precise position of these surface structures is determined by means of the pattern recognition method, and the positional relationship between the first 3D model and second 3D model is determined therefrom.

Advantageously, the contact areas of the contact pattern can depict local correspondences between the first 3D model and the second 3D model.

The contact areas hence arise from the contact between the tooth protuberances and tooth fissures in the upper jaw and lower jaw in the closed-bite position and accordingly correlate to local correspondences which enable the positional relationship between the two 3D models to be determined.

Advantageously, the first 3D model and/or the second 3D model can be deformed or aligned with use of the determined geometric positional relationship in order to minimize a first deviation between first virtual contact areas on the first 3D model and second virtual contact areas on the second 3D model, and/or to minimize a second deviation between the arrangement of a first virtual surface structure of the first 3D model relative to a second virtual surface structure of the second 3D model and the arrangement of the corresponding first surface structure of the upper jaw relative to the corresponding second surface structure of the lower jaw from the lateral image.

The registration error and/or calibration error can cause the first 3D model and second 3D model to be distorted or shifted in comparison to the actual dimensions of the measured object. This leads to the first deviation between contact areas in comparison to the contact pattern, and to the second deviation of the virtual surface structures in comparison to the lateral image. To correct this measuring error, the first 3D model and/or the second 3D model are distorted or deformed such that the contact conditions arising from the contact pattern and the conditions arising from a lateral image, or from a number of lateral images, are satisfied. The first deviation and second deviation are thereby minimized as much as possible. For example, the minimization method of the sum of error squares can be used therefor. The first 3D model or second 3D model can be deformed by means of a deformation method in which the respective 3D model is divided into different sections which are connected to each other by simulated springs. The simulated spring forces of the springs cause the deformation to be evenly distributed to these sections, and the respective 3D model is flexibly deformed. These sections can for example be the individual optical three-dimensional images which were combined into the respective 3D model.

Advantageously, the first 3D model and/or the second 3D model can be deformed with the aid of the determined geometric positional relationship, such that the first virtual contact areas on the first 3D model correspond with the second virtual contact areas on the second 3D model, and/or such that the first virtual surface structure of the first 3D model is arranged relative to the second virtual surface structure of the second 3D model, and the corresponding first surface structure of the upper jaw is arranged relative to the corresponding second surface structure of the lower jaw from the lateral image.

The measuring error arising from the registration error and calibration error is thereby completely corrected.

Advantageously, the second 3D model that has a higher measuring precision the first 3D model can remained unchanged, and the first 3D model can be deformed to adapt to the second 3D model.

A check is performed of whether the criteria are sufficient for successful registration. It can thereby be ascertained that the first 3D model or the second 3D model has a smaller registration error and hence a greater measuring precision than the second 3D model or the first 3D model. Subsequently, the more precise 3D model remains unchanged, and the more imprecise 3D model is adapted thereto. As a result, the deviation between the 3D models and the actual dimensions of the object is extremely small after the adaptation.

Advantageously, the first 3D model that has a higher measuring precision than the second 3D model can remained unchanged, and the second 3D model can be deformed to adapt to the first 3D model.

Advantageously, the individual images of the first 3D model and second 3D model can be recorded using a global registration. In the global registration, each image to be recorded is recorded both with a previous image as well as with another already made image in order to lessen a registration error. The image to be recorded, the previous image, and additional image have common overlapping areas. The additional image can be the pre-previous image, or an image taken before that in the image series.

The registration error is reduced by means of the global registration in that each image is not just compared with the previous image, but rather also with additional images with which it possesses common overlapping areas. In the registration of the particular image with the previous image and other images taken before then, contradictions in the positional relationship can arise that are ascribable to registration error and/or calibration error. To determine the actual positional relationships, an average of the positional relationships can be calculated from the registration of the previous image and other images to mutually cancel the contradictions and minimize the global registration error.

BRIEF DESCRIPTION OF THE DRAWINGS

The invention will be explained with reference to the drawings. In the figures.

EXAMPLE

Figure 1:
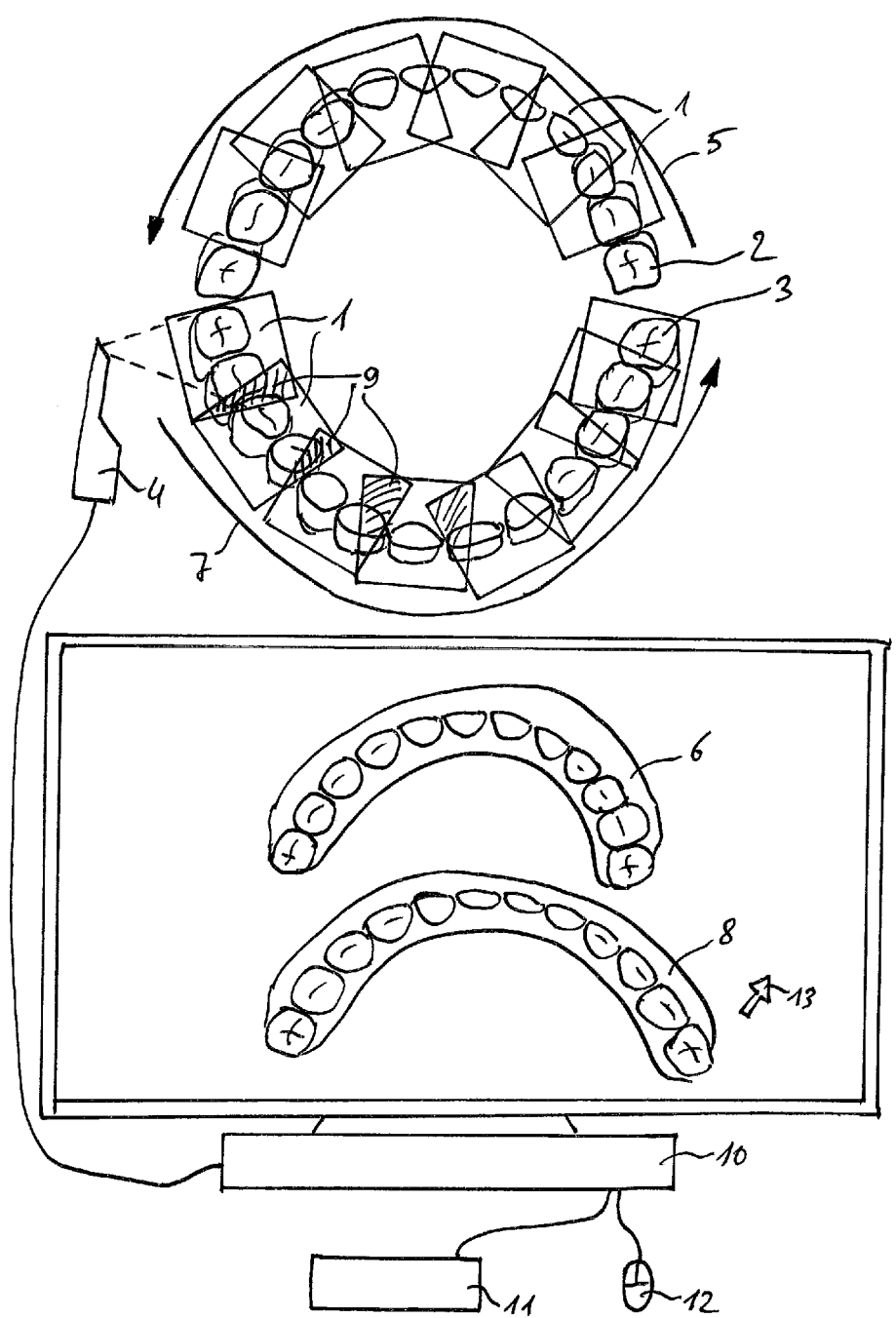
FIG. 1 shows a sketch to illustrate the existing method for registration.

FIG. 1 shows a sketch to illustrate the present method for recording individual three-dimensional optical images 1 to form a global image of a tooth situation comprising an upper jaw 2 and a lower jaw 3. During the measurement, a digital camera that is based on a strip projection method or a confocal optical method is moved in a first step along a first direction of movement 5 around the upper jaw 2 in order to measure a first 3D model 6, and then in a second step along a second direction of movement 7 around the lower jaw 3 in order to measure a second 3D model 8. During the measurement, the three-dimensional optical images are generated at regular intervals in time. The individual images can for example be generated at a cyclical frequency between 10 Hz and 20 Hz. Then the individual images 1 are recorded with each other using the overlapping areas 9 that are depicted in dashed lines and combined into the first 3D model 6 and second 3D model 8.

A computer 10 records the measured data of the digital camera 4, calculates the individual images 1, records the individual images 1, and combines the individual images into the first 3D model 6 and second 3D model 8. The user has the option of moving and rotating the first 3D model 6 and second 3D model 8 by means of a cursor using input means such as a keyboard 11 and a mouse 12 in order to change the direction of observation.

The first 3D model 6 and first 3D model 8 can comprise the entire upper jaw or lower jaw, or only a subsection.

To generate the global image of the tooth situation, it is then necessary to determine a geometric positional relationship between the first 3D model 6 and the second 3D model 8.

Figure 2:
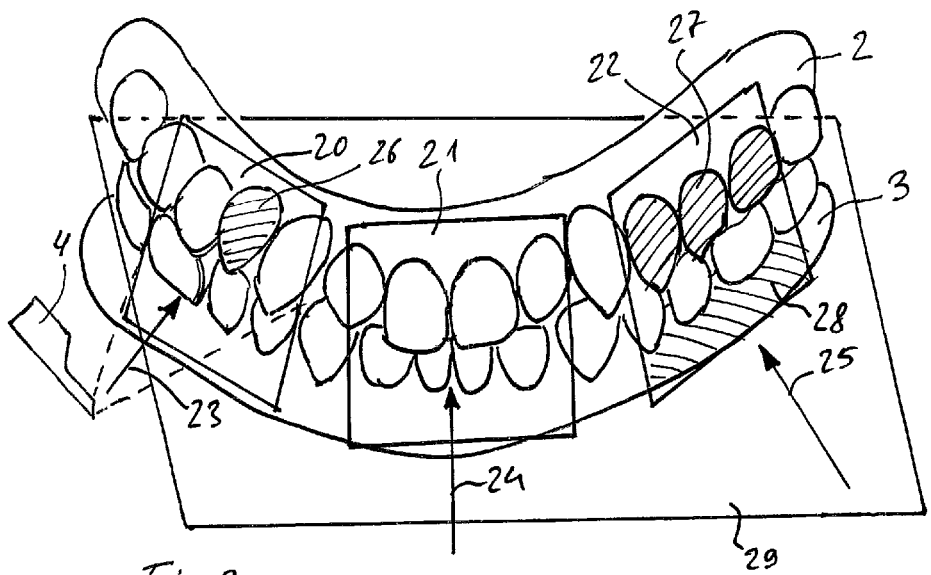
FIG. 2 shows a sketch to illustrate the determination of the geometric positional relationship between the 3D models.

FIG. 2 shows a sketch to illustrate the determination of the geometric positional relationship between the 3D models 6 and 8. By using the dental camera 4 from FIG. 1, additional lateral images 20, 21 and 22 generated from a first image direction 23, a second image direction 24 and a third image direction 25. The lateral images 20 and 22 are hence taken from a buccal direction in the area of tooth pairs 16-46 and 26-36 according to the FDI notation. The second lateral image 21 is hence made from a buccal direction in the area of tooth pairs 11-41 and 21-31 according to the FDI notation. Then the lateral images 20, 21 and 22 are searched using a pattern recognition method by means of the computer 10 from FIG. 1 for a first surface structure of the first 3D model and for second surface structure from the second 3D model. The first surface structure or second surface structure can be an individual tooth 26 which in the present case corresponds to tooth 14 according to the FDI notation, a group of teeth 27 that are depicted with dashed lines, and teeth 24, 25 and 26 according to the FDI notation, or a characteristic structure 28 of the gingiva. The positional relationship between the first 3D model 6 and the second 3D model 8 can be determined by using the arrangement of the first surface structure 26, 27 relative to the second surface structure 28 in lateral images 20, 21 and 22. If the first 3D model 6 and/or the second 3D model 8 are distorted by a registration error or calibration error, the different lateral images 20, 21 and 22 may provide different, contradictory positional relationships. These contradictions can be used to correct the first 3D model 6 and/or second 3D model 8 in order to generate an error-free global image.

In addition to the lateral images, an occlusion paper 29 can be placed between the upper jaw 2 and lower jaw 3. Then the upper jaw 2 and lower jaw 3 are brought into the depicted closed-bite position, wherein a colored layer of occlusion paper 29 colors certain contact areas between the upper jaw 2 and lower jaw 3. As in the depicted instance, the occlusion paper 29 can consist of an individual sheet or several strips that are clamped between the upper jaw 2 and lower jaw 3.

After the contact areas have been marked with the occlusion paper 29, the upper jaw 2 and lower jaw 3 are measured as depicted in FIG. 1, wherein the first 3D model 6 and the second 3D model are generated with the marked contact areas.

Figure 3:
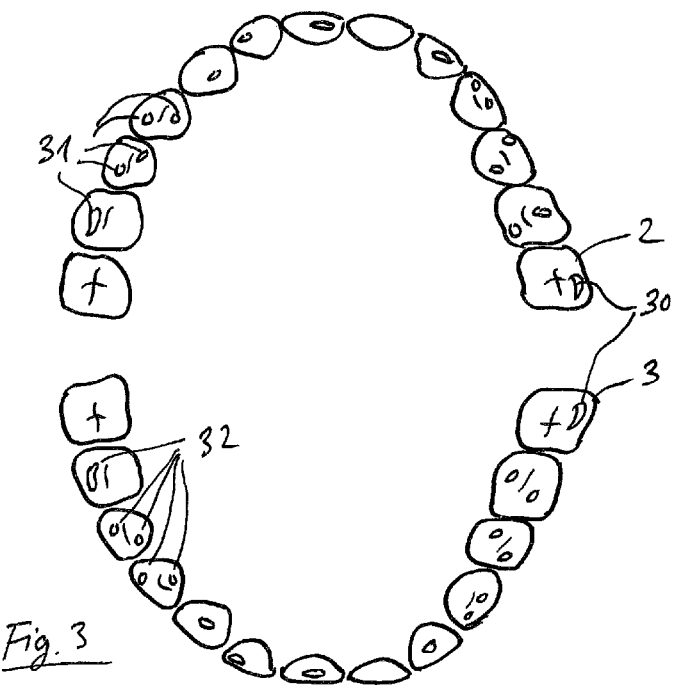
FIG. 3 shows the upper jaw and lower jaw from the occlusal direction after marking the contact areas.

FIG. 3 shows the upper jaw 2 and lower jaw 3 from the occlusal direction after marking the contact areas 30 using the occlusion paper. The first contact areas 31 on the upper jaw 2 correspond to the second contact areas 32 on the lower jaw 3. The first contact areas 31 and corresponding second contact areas 32 constitute local correspondences that enable the geometric positional relationships to be determined between the first 3D model of the upper jaw 2 and the second 3D model of the lower jaw 3.

Figure 4:
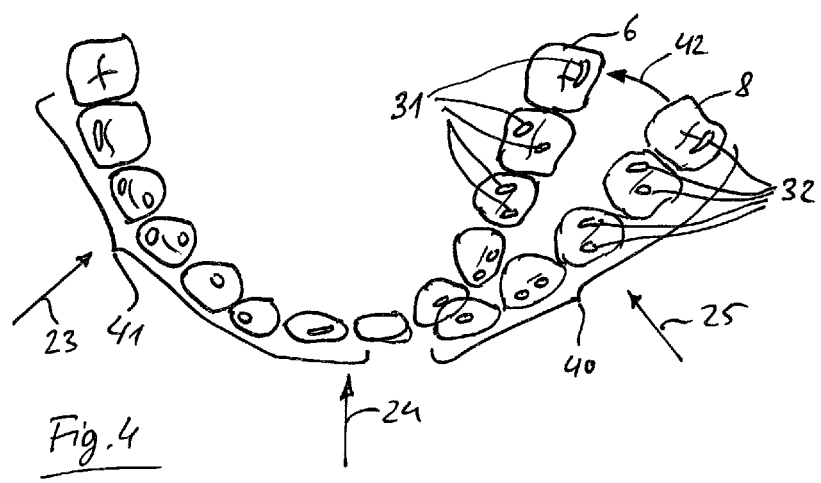
FIG. 4 shows the first 3D model of the upper jaw and the second 3D model of the lower jaw with a registration error.

FIG. 4 shows a sketch of the first 3D model 6 of the upper jaw 2 and the second 3D model 8 of the lower jaw 3, wherein the second 3D model 8 significantly deviates from the first 3D model in one area 40 due to a registration error and/or a calibration error. In one area 41, the first 3D model 6 was brought into correspondence with the second 3D model 8. The arrows designate the imaging directions 23, 24 and 25 for the lateral images. The first contact areas 31 hence deviate significantly in the first area 40 from the second contact areas 32 of the second 3D model 8, wherein the first contact areas 31 are brought into correspondence with the second contact areas 32 in the second area. In addition to the contact areas 31 and 32, the lateral images 23 and 24 can also be used to determine the positional relationship and to overlap the two 3D models 6 and 8 in the area 41.

To correct the registration error and/or the calibration error, the second 3D model 8 is deformed along a deformation direction 42 such that a first deviation between the first contact areas on the first 3D model 6 and second contact areas 32 on the second 3D model 8 is minimized. As an additional criterion for the correction, the lateral image 25 can also be used, wherein a second deviation between the arrangement of a first virtual surface structure 27 of the first 3D model 6 relative to a second virtual surface structure 28 of the second 3D model 8 is minimized by arranging the corresponding surface structures 27 and 28 on the lateral image 25. In this optimization process, the least squares method can be used, for example.

In the present case, the first 3D model has a greater measuring precision such that the second 3D model 8 subject to the registration error is adapted to the first 3D model 6 along deformation direction 42.

Alternately, the second 3D model 8 can remain unchanged, and the first 3D model 6 can be adapted thereto.

Conditions from the lateral images 23, 24 and 25 as well as the conditions from the differences of contact areas 31 and 32 are hence used, in order to correct the registration error and/or calibration error by means of a minimization method.

Figure 5:
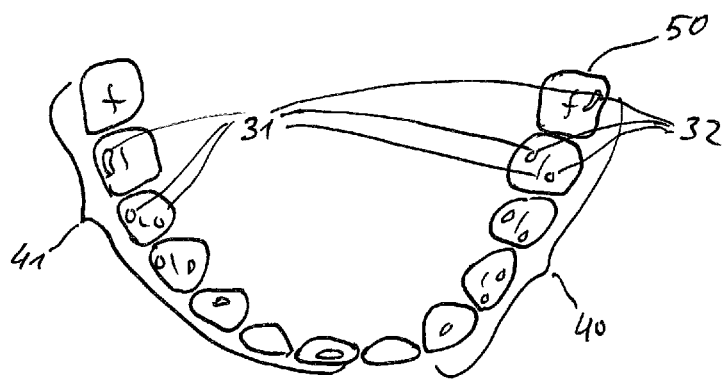
FIG. 5 shows the result of the correction from FIG. 4.

FIG. 5 shows the result of the correction from FIG. 4, wherein the first contact areas 31 of the first 3D model 6 and the second contact areas 32 of the second 3D model 8 are caused to overlap both in the first area 40 as well as in the second area 41. The result of the method is hence a global image 50 comprising the first 3D model 6 and the second 3D model 8 which were adapted to each other by means of the contact areas 31 and 32 as well by means of the lateral images 23, 24 and 25 in order to eliminate the registration error.

REFERENCE CHARACTERS

1 Individual three-dimensional optical images
2 Upper jaw
3 Lower jaw
4 Dental camera
5 First direction of movement
6 First 3D model
7 Second direction of movement
8 Second 3D model
9 Overlapping areas
10 Computer
11 Keyboard
12 Mouse
13 Cursor
20-22 Lateral images
23 First image direction
24 First image direction
25 Third image direction
26 Individual tooth
27 Group of teeth
28 Characteristic structure of the gingiva
29 Occlusion paper
30 Markings of the contact areas
31 First contact areas
32 Second contact areas
40 First area
41 Second area
42 Deformation direction
50 Global image

The invention claimed is:

1. A method, comprising the steps of:
generating a first 3D model of a first subsection of an upper jaw from a portion of a plurality of three-dimensional optical images;
generating a second 3D model of a second subsection of a lower jaw from another portion of the plurality of three-dimensional optical images;
determining a geometric relationship between the first 3D model and the second 3D model based on
   i. a lateral three-dimensional optical image or
   ii. a lateral three-dimensional optical image and a contact pattern,
wherein the lateral three-dimensional optical image has an image area which at least partially comprises the first subsection of the upper jaw and at least partially comprises the second subsection of the lower jaw, and
wherein the contact pattern comprises a plurality of contact areas between the upper jaw and lower jaw, and
deforming the first 3D model and/or the second 3D model based on the determined geometric positional relationship, said deforming step including the step of dividing each 3D model into different sections which are connected to each other by simulated spring forces, said simulated spring forces causing the deformation to be evenly distributed to the different sections of each 3D model.

2. The method according to claim 1, wherein, in the determining, a plurality of lateral three-dimensional optical images are used to determine the geometric positional relationship.

3. The method according to claim 1, wherein the determining is based on the lateral three-dimensional optical image, and
wherein, in the determining, the lateral three-dimensional optical image is searched for (i) a first surface structure of the first 3D model and (ii) a second surface structure of the second 3D model, and
wherein the geometric positional relationship between the first 3D model and the second 3D model is determined based on an arrangement of the first surface structure relative to the second surface structure.

4. The method according to claim 1, wherein the determining is based on the contact pattern, and
wherein the plurality of contact areas respectively correspond to a plurality of local correspondences between the first 3D model and the second 3D model.

5. The method according to claim 1,
wherein the first 3D model and/or the second 3D model are adjusted such that first virtual contact areas on the first 3D model correspond with second virtual contact areas on the second 3D model.

6. The method according to claim 1, wherein the first 3D model and/or the second 3D model are adjusted such that a first virtual surface structure of the first 3D model is arranged relative to a second virtual surface structure of the second 3D model.

7. The method according to claim 1, wherein one of the first 3D model and the second 3D model has a greater measuring precision than another of the first 3D model and the second 3D model, and
wherein the other of the first 3D model and the second 3D model is adjusted relative to the one of the first 3D model and the second 3D model with the greater measuring precision.

8. The method according to claim 1, wherein the first 3D model and/or the second 3D model are adjusted such that a deviation between first virtual contact areas on the first 3D model and second virtual contact areas on the second 3D model is minimized.

9. The method according to claim 1, wherein the first 3D model and/or the second 3D model are adjusted such that a deviation between a first virtual surface structure of the first 3D model and a second virtual surface structure of the second 3D model is minimized.

10. The method according to claim 1, wherein each of the plurality of three-dimensional optical images overlaps with at least two other images of the plurality of three-dimensional optical images and is registered with the at least two other images of the plurality of three-dimensional optical images and wherein the at least two other images of the plurality of three-dimensional optical images comprise a previous image and another already made image.

11. The method according to claim 1, further comprising taking the lateral three-dimensional optical image from a labial or a buccal direction or from an oblique direction that is at a maximum angle of 30° to the labial direction.

12. An apparatus, comprising:
a computer, configured to:
generate a first 3D model of a first subsection of an upper jaw from a portion of a plurality of three-dimensional optical images,
generate a second 3D model of a second subsection of a lower jaw from another portion of the plurality of three-dimensional optical images, and
determine a geometric positional relationship between the first 3D model and the second 3D model based on
i. a lateral three-dimensional optical image or
ii. a lateral three-dimensional optical image and a contact pattern,
wherein the lateral three-dimensional optical image has an image area which at least partially comprises the first subsection of the upper jaw and at least partially comprises the second subsection of the lower jaw, and
wherein the contact pattern comprises a plurality of contact areas between the upper jaw and lower jaw, and
wherein the computer is further configured to deform the first 3D model and/or the second 3D model based on the determined geometric positional relationship by dividing each 3D model into different sections which are connected to each other by simulated spring forces, said simulated spring forces causing the deformation to be evenly distributed to the different sections.

13. The apparatus according to claim 12, wherein the computer is further configured to determine the geometric positional relationship based on a plurality of lateral three-dimensional optical images.

14. The apparatus according to claim 12, wherein the computer is further configured to search the lateral three-dimensional optical image for (i) a first surface structure of the first 3D model and (ii) a second surface structure of the second 3D model, and
wherein the computer is further configured to determine the geometric positional relationship between the first 3D model and the second 3D model based on an arrangement of the first surface structure relative to the second surface structure.

15. The apparatus according to claim 12, wherein the plurality of contact areas respectively correspond to a plurality of local correspondences between the first 3D model and the second 3D model.

16. The apparatus according to claim 12, wherein the computer is further configured to adjust the first 3D model and/or the second 3D model such that first virtual contact areas on the first 3D model correspond with second virtual contact areas on the second 3D model.

17. The apparatus according to claim 12, wherein the computer is further configured to adjust the first 3D model and/or the second 3D model such that a first virtual surface structure of the first 3D model is arranged relative to a second virtual surface structure of the second 3D model.

18. The apparatus according to claim 12, wherein one of the first 3D model and the second 3D model has a greater measuring precision than another of the first 3D model and the second 3D model, and
wherein the other of the first 3D model and the second 3D model is adjusted relative to the one of the first 3D model and the second 3D model with the greater measuring precision.

19. The apparatus according to claim 12, wherein the computer is further configured to adjust the first 3D model and/or the second 3D model such that a deviation between first virtual contact areas on the first 3D model and second virtual contact areas on the second 3D model is minimized.

20. The apparatus according to claim 12, wherein the computer is further configured to adjust the first 3D model and/or the second 3D model such that a deviation between a first virtual surface structure of the first 3D model and a second virtual surface structure of the second 3D model is minimized.

21. The apparatus according to claim 12, wherein each of the plurality of three-dimensional optical images overlaps with at least two other images of the plurality of three-dimensional optical images, and
wherein the computer is further configured to register each of the plurality of three-dimensional optical images with the at the least two other images of the plurality of three-dimensional optical images, and
wherein the at least two other images of the plurality of three-dimensional optical images comprise a previous image and another already made image.

22. The apparatus according to claim 12, wherein said different sections are individual three dimensional optical images of said portion of the plurality of three-dimensional optical images and said another portion of the plurality of three-dimensional optical images.

* * * * *